(12) United States Patent
Eisler

(10) Patent No.: US 11,931,091 B2
(45) Date of Patent: Mar. 19, 2024

(54) PLASMA DISC REPAIR

(71) Applicant: Innovasis, Inc., Salt Lake City, UT (US)

(72) Inventor: Jesse Eisler, Vernon, CT (US)

(73) Assignee: Innovasis Inc., Salt Lake City, UT (US)

( * ) Notice: Subject to any disclaimer, the term of this patent is extended or adjusted under 35 U.S.C. 154(b) by 933 days.

(21) Appl. No.: 16/917,046

(22) Filed: Jun. 30, 2020

(65) Prior Publication Data

US 2020/0405769 A1 Dec. 31, 2020

Related U.S. Application Data

(60) Provisional application No. 62/868,959, filed on Jun. 30, 2019.

(51) Int. Cl.
| | |
|---|---|
| *A61B 17/32* | (2006.01) |
| *A61B 18/04* | (2006.01) |
| *A61B 1/313* | (2006.01) |
| *A61B 18/00* | (2006.01) |
| *A61B 18/02* | (2006.01) |

(52) U.S. Cl.
CPC ............ *A61B 18/042* (2013.01); *A61B 1/313* (2013.01); *A61B 1/3135* (2013.01); *A61B 2018/00184* (2013.01); *A61B 2018/00202* (2013.01); *A61B 2018/00339* (2013.01); *A61B 2018/0293* (2013.01)

(58) Field of Classification Search
CPC ........ A61B 18/042; A61B 2018/00202; A61B 2018/00339
See application file for complete search history.

(56) References Cited

U.S. PATENT DOCUMENTS

2012/0040308 A1* 2/2012 Holbeche ............. A61C 1/0015
433/89

* cited by examiner

*Primary Examiner* — Laura A Bouchelle
(74) *Attorney, Agent, or Firm* — Brooks, Cameron & Huebsch, PLLC

(57) ABSTRACT

The present disclosure includes devices and methods of treating a herniated disc comprising treating an opening in a vertebral disc by applying plasma to the vertebral disc, wherein the vertebral disc comprises a nucleus portion and an outer annulus fibrosus portion, and wherein the plasma seals the opening in the vertebral disc. The devices and method comprises a plasma delivery device configured to be handheld and used percutaneously or in minimally invasive surgery. The vertebral disc, which comprises a nucleus pulposus and an outer annulus fibrosus, can be herniated with a rupture caused by a tear or opening in the annulus fibrosus, that can be repaired when the annulus fibrosus is sealed by the use of the plasma.

19 Claims, 3 Drawing Sheets

PLASMA DISC REPAIR

PRIORITY INFORMATION

This application claims priority of U.S. Provisional Application Ser. No. 62/868,959, filed on Jun. 30, 2019, the contents of which are incorporated herein by reference.

TECHNICAL FIELD

This disclosure relates to methods and apparatus for the repair of vertebral discs, more specifically related to method and apparatus for the repair of vertebral discs using plasma.

BACKGROUND

The bones (vertebrae) that form the spine in the back are cushioned by small discs. The vertebral discs are round and flat with a tough, outer layer (annulus) that surrounds a jellylike material called the nucleus. Located between each of the vertebra in the spinal column, discs act as shock absorbers for the spinal bones.

A herniated disc (also called a bulged, slipped or ruptured) is a fragment of the disc nucleus that is pushed out of the annulus into the spinal canal through a tear or rupture in the annulus. Discs that become herniated usually are in an early stage of degeneration. The spinal canal has limited space, which is inadequate for the spinal nerve and the displaced herniated disc fragment. Due to this displacement, the disc presses on spinal nerves, often producing pain, which may be severe.

Patients with herniated disks may have various symptoms. If the herniated disc is not pressing on a nerve, the patient may experience a low backache or no pain at all. If it is pressing on a nerve, there may be pain, numbness, or weakness in the area of the body to which the nerve travels. Typically, a herniated disc is preceded by an episode of low back pain or a long history of intermittent episodes of low back pain.

Some herniated discs do not require surgery, however, a small percentage of people with herniated, degenerated discs may experience symptomatic or severe and incapacitating low back pain, which significantly affects daily life.

The initial treatment for a herniated disc is usually conservative and nonsurgical. A herniated disc frequently is treated with nonsteroidal anti-inflammatory medication if the pain is only mild to moderate. An epidural steroid injection may be performed utilizing a spinal needle under X-ray guidance to direct the medication to the exact level of the disc herniation. A physician may recommend surgery if conservative treatment options, such as physical therapy and medications, do not reduce or end the pain altogether. Surgical options include: artificial disc surgery which is a surgical replacement of a diseased or herniated lumbar disc with a manufactured disc; discectomy which is a surgical removal or partial removal of an intervertebral disc; laminectomy which is a surgical removal of most of the bony arch, or lamina, of a vertebra; laminotomy which is an opening made in a lamina to relieve pressure on the nerve roots; or spinal fusion which is a procedure in which bone is grafted onto the spine, creating a solid union between two or more vertebrae.

With some patients, the nonsurgical treatments are not an option and some patients may not wish to undergo surgery. Thus, a need for the treatment of bulging, herniated, and ruptured discs exist.

DETAILED DESCRIPTION

Figure 1A:
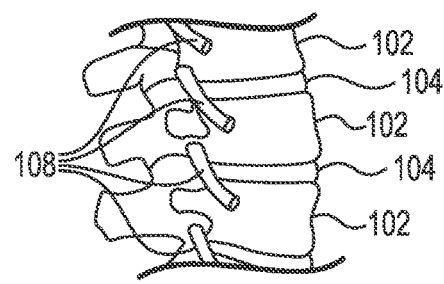
FIG. 1A illustrates a side view of a portion of a spine with normal discs.

The present disclosure includes devices and methods of treating a herniated disc comprising treating an opening in a vertebral disc by applying plasma to the vertebral disc, wherein the vertebral disc comprises a nucleus portion and an outer annulus fibrosus portion, and wherein the plasma seals the opening in the vertebral disc. The devices and method comprises a plasma delivery device configured to be handheld and used percutaneously or in minimally invasive surgery. The vertebral disc, which comprises a nucleus pulposus and an outer annulus fibrosus, can be herniated with a rupture caused by a tear or opening in the annulus fibrosus, that can be repaired when the annulus fibrosus is sealed by the use of the plasma. Embodiments of the present disclosure can be used to repair a herniated, bulging, and/or ruptured disc. In a number of embodiments, the opening in the vertebral disc annulus can be repaired through the use of plasma, include hot and/or cold plasma.

Plasma can be defined as a partially ionized gas which contains approximately equal numbers of positive and negative particles. Plasmas can be roughly classified into hot plasmas (also defined as near-equilibrium plasmas) and cold plasmas (or nonequilibrium plasmas). Hot plasmas are characterized by very high temperatures of electrons and heavy particles (atoms, molecules, or ions) and they are almost fully ionized. In cold plasmas, instead, the electron temperature is relatively high, while the translational energy of heavy particles remains very low, with temperature close to the room one and the ionization degree is typically low.

In a number of embodiments, a plasma delivery device (e.g., a cold plasma wand, a cold plasma pen, and/or a cold plasma pencil) can be used in a low- or minimally-invasive procedure to repair the disc annulus. By applying plasma to the disrupted annulus, the annulus can be repaired such that the disc nucleus is again sealed inside the annulus.

Various embodiments of the present invention will now be discussed with reference to the appended drawings. It is appreciated that these drawings depict only typical embodiments of the invention and are therefore not to be considered limiting of its scope.

Before describing various embodiments of the present disclosure in detail, it is to be understood that this disclosure is not limited to the parameters of the particularly exemplified implants, methods, systems and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the embodiments and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including implants, systems, processes, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "locking screw" includes one, two, or more locking screws.

As used herein, directional terms, such as "top," "bottom," "left," "right," "up," "down," "upper," "lower," "proximal," "distal," "vertical," "horizontal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible.

The figures herein follow a numbering convention in which the first digit or digits correspond to the figure number and the remaining digits identify an element or component in the figure. Similar elements or components between different figures can be identified by the use of similar digits. For example, 102 can reference element "02" in FIG. 1A, and a similar element can be referenced as 202 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. An element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

Furthermore, multiple instances of the same element may each include separate letters appended to the element number. For example, two instances of a particular element "20" may be labeled as "20*a*" and "20*b*". In that case, the element label may be used without an appended letter (e.g., "20") to generally refer to every instance of the element; while the element label will include an appended letter (e.g., "20*a*") to refer to a specific instance of the element.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein.

In an effort to provide patients will less invasive surgery, embodiments of the present disclosure include devices and methods for repairing vertebral discs with low or minimally invasive surgery.

Vertebral discs are comprised of an inner section, the nucleus pulposus and a covering, the annulus fibrosus. The nucleus pulposus is the soft filling located in the center of the disc. It is contained by a strong covering consisting of 3 concentric layers of tough fibrous tissue of the annulus fibrosus.

With age, the intervertebral disk may lose fluid and become dried out. As this happens, the spongy disk (which is located between the vertebrae bones of the spine and acts as a "shock absorber") becomes compressed. This may lead to the breakdown of the tough outer ring (e.g., annulus fibrosus), allowing the nucleus, or the inside of the ring, to bulge out. This is called a bulging disk.

As the vertebral disc breaks down due to age or trauma, or with continued stress on the spine, the inner nucleus pulposus may actually rupture out from the annulus. This is a ruptured, or herniated, disk. The fragments of disc material can then press on the nerve roots located just behind the disk space. This can cause pain, weakness, numbness, or changes in sensation. Most disc herniations happen in the lower lumbar spine, especially between the fourth and fifth lumbar vertebrae and between the fifth lumbar vertebra and the first sacral vertebra (the L4-5 and L5-S1 levels). Embodiments of the present disclosure, however, can be used in the cervical, thoracic, lumbar, or sacral sections of the spine.

Cold plasma or cold atmospheric plasma can be nonthermal because it has electrons at a hotter temperature than the heavy particles that are at room temperature. Embodiments of the present disclosure can produce cold plasma via a number of methods, such as dielectric barrier discharge, atmospheric pressure plasma jet, plasma needle, and/or plasma pencil, among other. A number of gases can be used to produce cold plasma, such as helium, argon, nitrogen, heliox (a mix of helium and oxygen), and/or air, among others.

Embodiments of the present disclosure include a cold plasma delivery device that can coupled to a power supply or include a battery and may have a wand-like shape. The device can include a tip at the distal end of the wand-like device. The length and diameter of the device can vary depending on the desired size of the surface to be treated. No part of the device that is not generating plasma comes into direct contact with the disc. This helps minimize potential contamination or surface irritation. The cold plasma delivery device can be powered by AC, DC, or RF power.

While any gas can be used in the plasma delivery device, inert gases are preferred with helium being the most preferred.

Figure 1B:
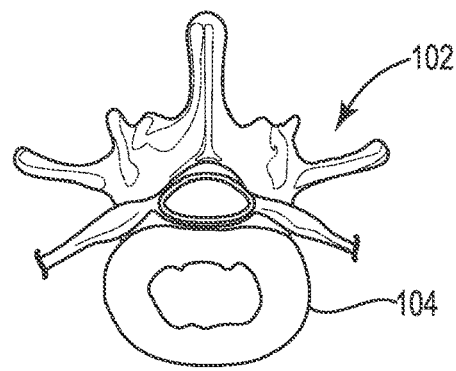
FIG. 1B illustrates a cross-sectional view of a portion of a spine with normal discs.

FIG. 1A illustrates a side view of a portion of a spine with normal discs. FIG. 1B illustrates a cross-sectional view of a portion of a spine with normal discs. The spine has vertebral bones 102 with a vertebral disc 104 on the top and bottom (e.g., between) of each bone. The spine also includes spinal nerves 108.

Figure 2A:
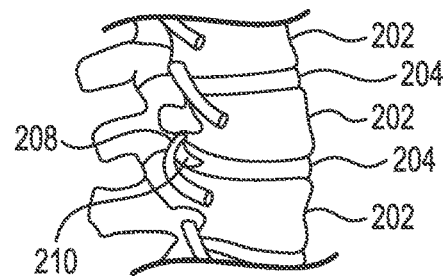
FIG. 2A illustrates a side view of a portion of a spine with a herniated disc.
Figure 2B:
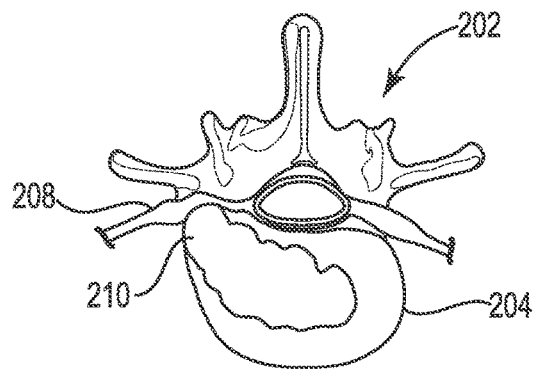
FIG. 2B illustrates a cross-sectional view of a portion of a spine with a herniated disc.

FIG. 2A illustrates a side view of a portion of a spine with a herniated disc. FIG. 2B illustrates a cross-sectional view of a portion of a spine with a herniated disc. The spine has vertebral bones 202 with a vertebral disc 204 on the top and bottom (e.g., between) of each bone. FIGS. 2A and 2B show a rupture or hernia 210 of the vertebral disc 204. The rupture or hernia 210 of the vertebral disc 204 can press on a spinal nerve 208 and can cause pain and discomfort.

Figure 3:
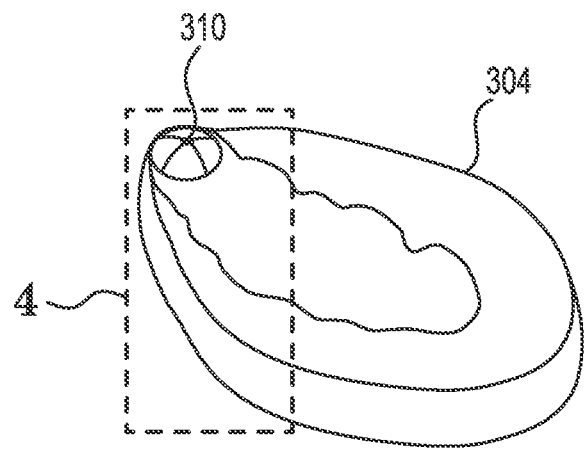
FIG. 3 illustrates an isometric view of a herniated disc.

FIG. 3 illustrates an isometric view of a herniated disc. FIG. 3 shows a herniated nucleus pulposus with an annular tear in the annulus fibrosus 310 of a vertebral disc 304. Embodiments of the present disclosure can be used to treat a herniated disc to close an opening in annulus fibrosis of the vertebral disc thus to keep the nucleus pulposus contained within the annulus fibrosus of the vertebral disc 304.

Figure 4:
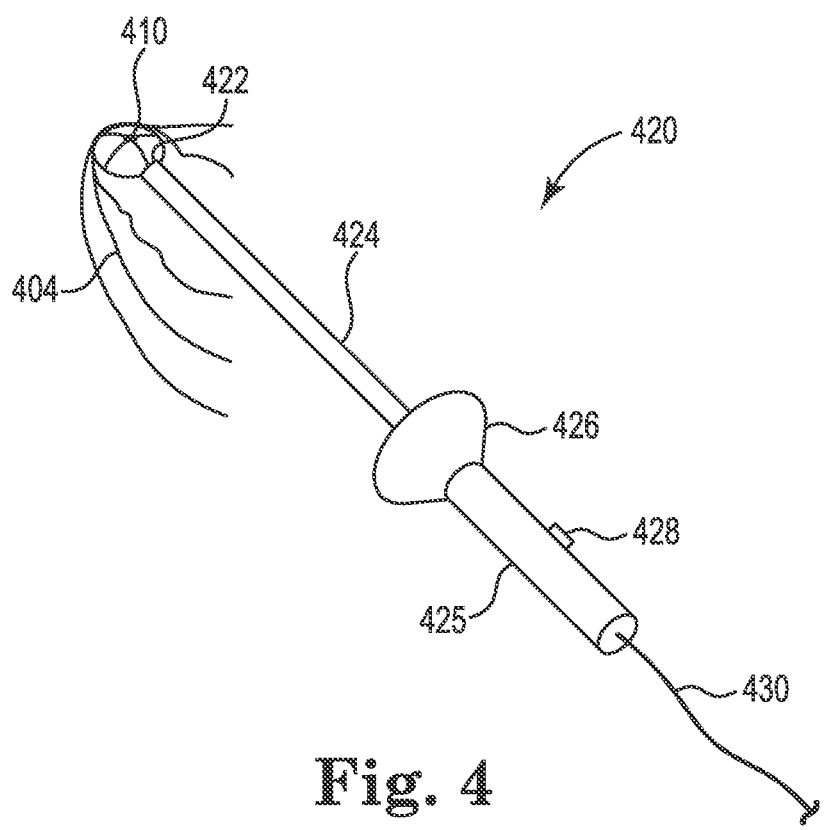
FIG. 4 illustrates a plasma delivery device treating a herniated disc according to embodiments of the present disclosure.

FIG. 4 illustrates a plasma delivery device treating a herniated disc according to embodiments of the present disclosure. FIG. 4 shows the annular tear 410 of a vertebral disc 404 being repaired with a plasma delivery device 420. The plasma delivery device 420 includes a discharge port 422 located at a distal end of a shaft 424. The port 422 and an amount of the shaft 424 can be placed inside the patient by the surgeon to repair the annular tear. The repair can be made via minimally invasive surgery, percutaneously, or through a cut down that exposes the vertebra. If required, a hollow working channel can be guided to the disc to provide access to the disc for the port 422 and shaft 424 portions of the plasma delivery device 420.

The plasma delivery device 420 may have a swivel portion 426 configured to aid in positioning the port 422 at the appropriate location when applying plasma to a disc. In some embodiments the swivel portion 426 couples shaft 424 to body portion 425 with a cylindrical rod that can turn freely within a support structure and allow movement with one degree of freedom where the shaft can rotate around a pivot point in one plane. The rod can be prevented from slipping out by a nut, washer or thickening of the rod.

The body 425 of the plasma deliver device 420 includes an on/off switch 428 and a power supply 430. In some embodiments, the plasma delivery device 420 can contain a battery or other contained power supply such that a power supply 430 is not needed. Alternating current (AC), direct current (DC), or radio frequency (RF) power can be used. When necessary, the body 425 will also include a reservoir for the gas used in the plasma generation. In some embodiments, this gas will be helium.

In some embodiments, the surgeon can use a pusher or other blunt instrument to gently push any exposed nucleus pulposus back into the annulus fibrosus.

In a number of embodiments, the plasma can seal the annular tears by gelling or thickening the surrounding tissue and that the plasma promotes cell reproduction in the annulus fibrosus, resulting in is a repaired disc with minimal surgery and no implant. In a number of embodiments, applying the plasma can cause tissue of the outer annulus fibrosus portion to gel.

In some embodiments, the entire plasma delivery device 420 can be sterilized. In some embodiments, the shaft 424 can be disconnected from the body 425 and the shaft 424 and port 422 can be disposable, and the body 425 can be resterilized.

In a number of embodiments, the method and apparatus of the present disclosure can be used to treat vertebral discs and other wounds, for example.

Figure 5A:
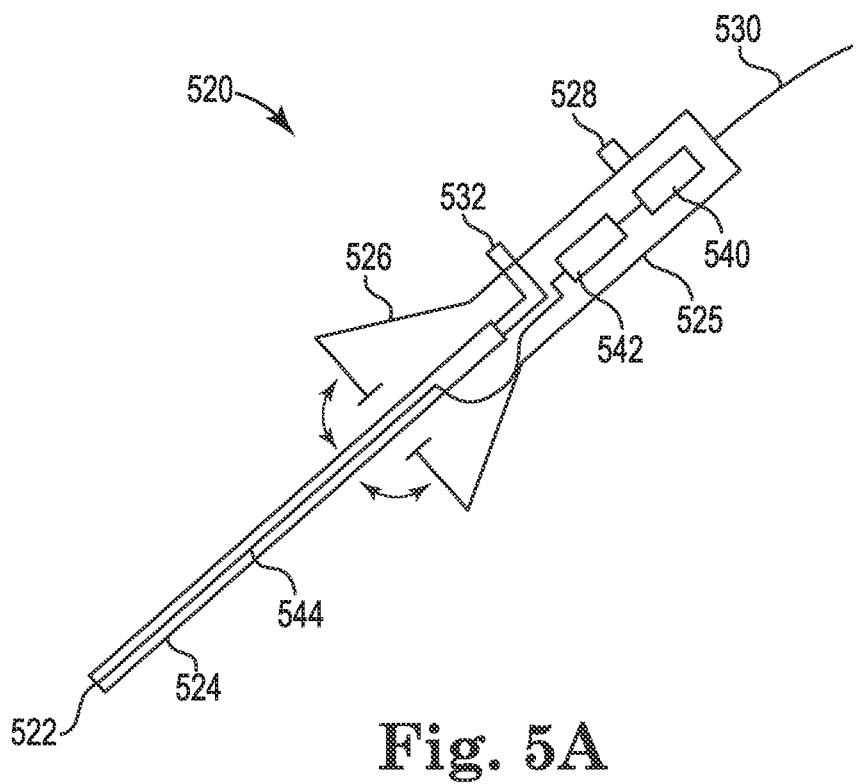
FIG. 5A illustrates a cross-sectional view of a plasma delivery device according to embodiments of the present disclosure.

FIG. 5A illustrates a cross-sectional view of a plasma delivery device according to embodiments of the present disclosure. At the distal end of the body 525, the plasma delivery device 520 may have a swivel portion 526 configured to aid in positioning the port 522 at the appropriate location when applying plasma to a disc. In some embodiments the swivel portion 526 couples shaft 524 to body portion 525 with a cylindrical rod that can turn freely within a support structure and allow movement with one degree of freedom where the shaft can rotate around a pivot point in one plane. The rod can be prevented from slipping out by a nut, washer or thickening of the rod.

The swivel portion 526 can control the swiveling and movement of the shaft 524 and port 522 via swivel control 532. Swivel control 532 can be located on the body 525 of the plasma delivery device 520. The body 525 can also include power switch 528 and power supply 530. Swivel control 532 can be directly coupled to swivel portion 526, where movement of the swivel control 532 causes movement of shaft 524 and port 522. Swivel control 532 can also include a micromotor and a joystick or finger pad coupled to the swivel portion 532, where the joystick or finger pad can be manipulated to cause the micromotor to cause movement of the shaft 524 and port 522.

Plasma delivery device 520 can include plasma generator 542 and gas reservoir 540. The plasma generator 542 can use gas stored in gas reservoir 540 to generate plasma that is sent through plasma delivery line 544 to port 522 to dispense and applying the plasma to the disc. Plasma generator 542 can include a dielectric barrier discharge, an atmospheric pressure plasma jet, a plasma needle, and/or a plasma pencil, among other plasma generating components. Gas reservoir 540 can include a pressurized cannister in the body portion. Gas reservoir 540 can include helium, argon, nitrogen, heliox, air, and mixtures thereof, among other gases, used to generate plasma.

Figure 5B:
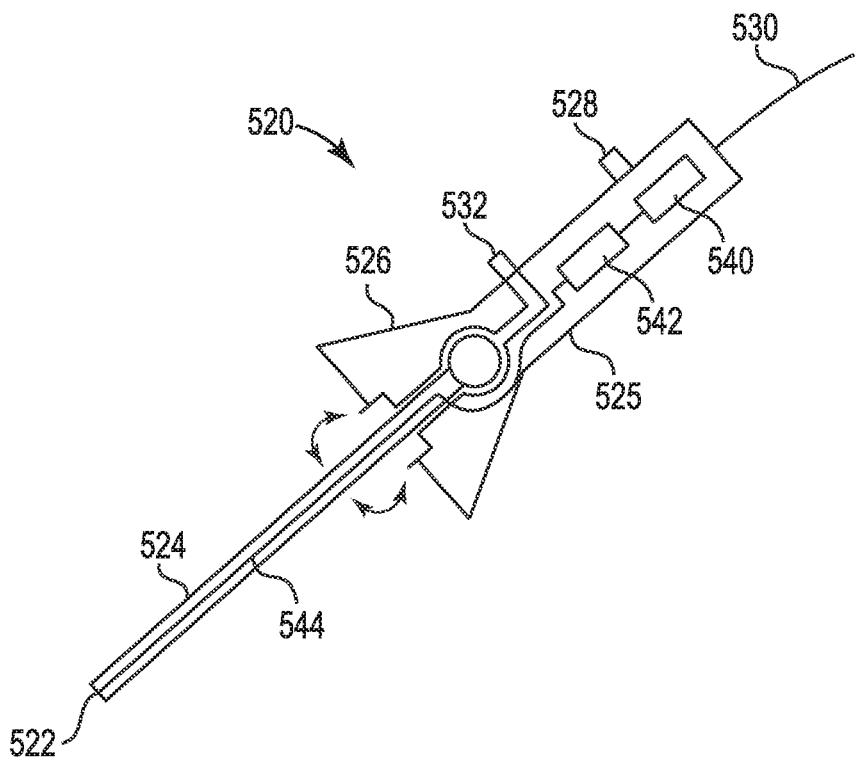
FIG. 5B illustrates a cross-sectional view of a plasma delivery device according to embodiments of the present disclosure.

FIG. 5B illustrates a cross-sectional view of a plasma delivery device according to embodiments of the present disclosure. At the distal end of the body 525, the plasma delivery device 520 may have a swivel portion 526 configured to aid in positioning the port 522 at the appropriate location when applying plasma to a disc. In some embodiments the swivel portion 526 couples shaft 524 to swivel portion 526, where a spherical proximal end of shaft 524 can turn freely within a support structure of swivel portion 526 and allow movement with three degrees of freedom where the shaft 524 can rotate within the swivel portion 526 in three planes.

The swivel portion 526 can control the swiveling and movement of the shaft 524 and port 522 via swivel control 532. Swivel control 532 can be located on the body 525 of the plasma delivery device 520. The body 525 can also include power switch 528 and power supply 530. Swivel control 532 can be directly coupled to swivel portion 526, where movement of the swivel control 532 causes movement of shaft 524 and port 522. Swivel control 532 can also include a micromotor and a joystick or finger pad coupled to the swivel portion 532, where the joystick or finger pad can be manipulated to cause the micromotor to cause movement of the shaft 524 and port 522.

Plasma delivery device 520 can include plasma generator 542 and gas reservoir 540. The plasma generator 542 can use gas stored in gas reservoir 540 to generate plasma that is sent through plasma delivery line 544 to port 522 to dispense and applying the plasma to the disc.

Plasma generator 542 can include a dielectric barrier discharge, an atmospheric pressure plasma jet, a plasma needle, and/or a plasma pencil, among other plasma generating components. Gas reservoir 540 can include a pressurized cannister in the body portion. Gas reservoir 540 can include helium, argon, nitrogen, heliox, air, and mixtures thereof, among other gases, used to generate plasma.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A method of treating a herniated disc comprising:
   treating an opening in a vertebral disc by applying plasma to the vertebral disc with a plasma delivery device comprising:
      a body portion configured to generate plasma;
      a shaft portion, wherein the shaft portion comprises a first end and a second end including a plasma delivery port configured to deliver the plasma generated by the body portion;
      a swivel portion, wherein the swivel portion is coupled to the body portion, wherein the first end of the shaft portion is coupled to a pivot point of the swivel portion configured to allow the shaft portion to rotate; and
      a swivel control, wherein the swivel control is directly coupled to the swivel portion and wherein movement of the swivel control causes movement of the shaft portion,
      wherein the vertebral disc comprises a nucleus portion and an outer annulus fibrosus portion, and wherein the plasma seals the opening in the vertebral disc.

2. The method of claim 1, further comprising pushing the nucleus portion of the vertebral disc inside the outer annulus fibrosus portion prior to applying the plasma to the vertebral disc.

3. The method of claim 1, further comprising applying the plasma with the plasma delivery device via percutaneous insertion into a vertebral space.

4. The method of claim 1, wherein applying the plasma causes tissue of the outer annulus fibrosus portion to gel.

5. The method of claim 4, wherein gelling of the tissue of the outer annulus fibrosus portion promotes cell reproduction in the outer annulus fibrosus portion.

6. The method of claim 1, further comprising treating the opening in the vertebral disc by accessing the vertebral disc percutaneously.

7. The method of claim 1, further comprising treating the opening in the vertebral disc by accessing the vertebral disc in a minimally invasive procedure.

8. A plasma delivery device comprising:
   a body portion configured to generate plasma;
   a shaft portion, wherein the shaft portion comprises a first end and a second end including a plasma delivery port configured to deliver the plasma generated by the body portion;
   a swivel portion, wherein the swivel portion is coupled to the body portion, wherein the first end of the shaft portion is coupled to a pivot point of the swivel portion configured to allow the shaft portion to rotate; and
   a swivel control, wherein the swivel control is directly coupled to the swivel portion and wherein movement of the swivel control causes movement of the shaft portion.

9. The device of claim 8, wherein the swivel portion connects the shaft portion to a distal end of the body portion.

10. The device of claim 8, wherein the body portion includes a gas reservoir and a plasma generator to generate plasma.

11. The device of claim 8, wherein the pivot point of the swivel portion allows the shaft portion to rotate with one degree of freedom.

12. The device of claim 8, wherein the pivot point of the swivel portion allows the shaft portion to rotate with three degrees of freedom.

13. The device of claim 8, wherein the plasma delivery port is configured to deliver the plasma to a vertebral disc.

14. A plasma delivery device comprising:
   a body portion;
   a swivel portion attached to the body portion;
   a shaft sized to be percutaneously inserted to a position adjacent to a vertebral disc, the shaft comprising:
      a first end connected to the rotatable swivel; and
      a second end comprising a plasma delivery port;
   a gas reservoir as gas source;
   a plasma generator located in the body portion and in communication with the gas reservoir, the shaft, and the plasma delivery port; and a swivel control, wherein the swivel control is directly coupled to the swivel portion and wherein movement of the swivel control causes movement of the shaft.

15. The plasma delivery device of claim 14, wherein the plasma generator includes at least one of dielectric barrier discharge, atmospheric pressure plasma jet, plasma needle, and plasma pencil.

16. The plasma delivery device of claim 14, wherein the gas reservoir is a pressurized cannister in the body portion.

17. The plasma delivery device of claim 14, wherein the gas reservoir comprises helium, argon, nitrogen, heliox, air, and mixtures thereof.

18. The plasma delivery device of claim 14, wherein the plasma delivery port is configured to deliver plasma to the from the has reservoir to the vertebral disc.

19. The plasma delivery device of claim 14, further comprising an energy source for the plasma generator, wherein the energy source comprising a power cord coupled to an electrical outlet or a rechargeable battery.

* * * * *